United States Patent
Gutkovich (12)

(10) Patent No.: US 10,194,876 B1
(45) Date of Patent: Feb. 5, 2019

(54) GAMMA CAMERA WITH INCREASED RESOLUTION

(71) Applicant: Vitaly Gutkovich, Nesher (IL)

(72) Inventor: Vitaly Gutkovich, Nesher (IL)

(73) Assignee: Vitaly Gutkovich, Nesher (IL)

(*) Notice: Subject to any disclaimer, the term of this patent is extended or adjusted under 35 U.S.C. 154(b) by 0 days.

(21) Appl. No.: 15/844,549

(22) Filed: Dec. 17, 2017

(51) Int. Cl.
  *G01T 1/20* (2006.01)
  *A61B 6/00* (2006.01)

(52) U.S. Cl.
  CPC .......... *A61B 6/4258* (2013.01); *A61B 6/4458* (2013.01); *A61B 6/503* (2013.01); *A61B 6/547* (2013.01)

(58) Field of Classification Search
  CPC ...... G01T 1/1648; G01T 1/2928; G01T 1/243
  See application file for complete search history.

(56) References Cited

U.S. PATENT DOCUMENTS

| | | | | |
|---|---|---|---|---|
| 3,793,520 A | * | 2/1974 | Grenier | G01T 1/1644 250/363.02 |
| 5,847,398 A | * | 12/1998 | Shahar | G01T 1/1648 250/370.09 |
| 8,269,180 B2 | * | 9/2012 | De Geronimo | G01T 1/247 250/370.01 |
| 2007/0078339 A1 | * | 4/2007 | Andress | A61B 6/463 600/436 |
| 2011/0150311 A1 | * | 6/2011 | Bond | G06T 7/33 382/131 |
| 2016/0213250 A1 | * | 7/2016 | Su | A61B 3/125 |

OTHER PUBLICATIONS

Lee et al., "Development of a motorized variable angle slant-hole collimator," 2015, IEEE Nuclear Science Symposium and Medical Imaging Conference, 3 pages.*

* cited by examiner

*Primary Examiner* — Kiho Kim
(74) *Attorney, Agent, or Firm* — Pearl Cohen Zedek Latzer Baratz LLP

(57) ABSTRACT

A gamma camera includes a detector array of a plurality of detector pixels. Each detector pixel is configured to generate a signal indicative of gamma or x-ray radiation incident on that detector pixel. Each collimator of a collimator array is configured to collimate the radiation onto a detector pixel. An actuator is configured to move the collimator array along an axis in one or a plurality of incremental movements, each incremental movement smaller than a lateral dimension of a detector pixel along that axis. A processor is configured to obtain the signals generated by each detector pixel of the plurality of detector pixels and to generate image data with sub-pixel resolution from the sampled signals and a position of the collimator when each signal was generated.

18 Claims, 5 Drawing Sheets

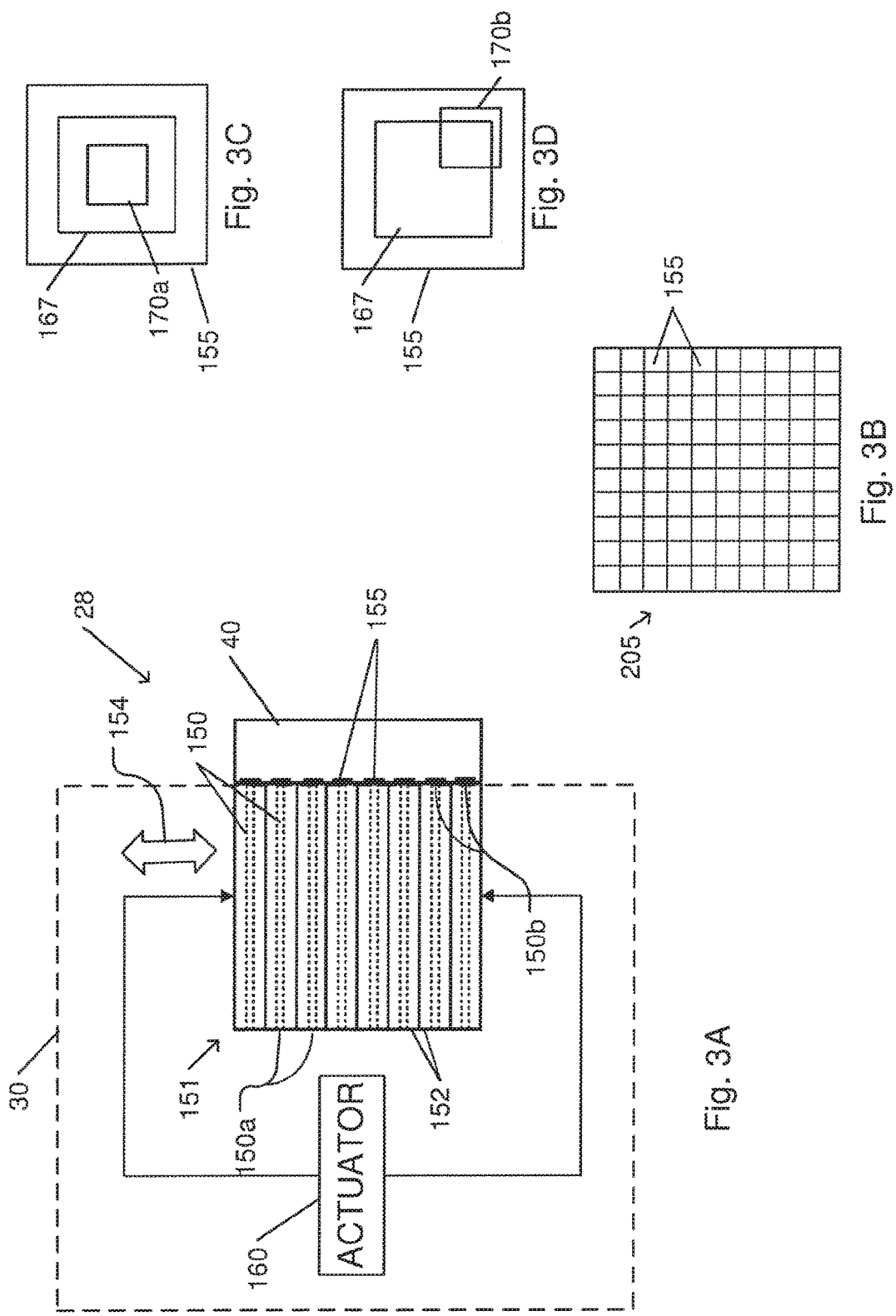

GAMMA CAMERA WITH INCREASED RESOLUTION

FIELD OF THE INVENTION

The present invention relates to medical imaging, and more particularly to a gamma camera with increased resolution.

BACKGROUND OF THE INVENTION

Intraoperative angiography is a medical imaging technique used to visualize the inside, or lumen, of blood vessels and organs with particular interest to the arteries, veins, and the heart chambers during a cardiac operation procedure.

Intraoperative fluorescence imaging (IFI), may be used to verify tumor removal in oncological pathologies. Use of IFI to assess myocardial perfusion intraoperatively after off-pump cardiac artery bypass graft (OPCABG) surgery has been clinically tested. This procedure may involve the injection of fluorescent tracers into the venous system of the patient during the surgery, and excitation of the tracers with a near-infrared laser light source. Currently, IFI system may be used for assessment of the grafts. However, since the photons emitted in fluorescence applications are highly absorbed in tissue (unlike gamma photons), the IFI signals are reduced when the target is covered by a layer of tissue (intramyocardial arteries).

High frequency handheld ultrasound systems have been investigated for use in OPCABG to detect the intramuscular left anterior descending (LAD) coronary arteries during OPCABG. This method may provide poor image quality for on-pump cardiac artery bypass graft (CABG) and coronary arteries other than the LAD during OPCABG, if at all accessible to the system.

Conventional, as well as hand held diagnostic nuclear imaging, may identify radionuclide distribution in a subject, such as a human patient. Typically, one or more radiopharmaceuticals or radioisotopes are injected into the subject's blood system. This results in a relatively high whole body radiation dose. Even specifically binding tracers that concentrate in specific areas within the tissue may travel to all tissues of the patient's body. A typical minimum effective radiation dose may range from 2.2 mSv to more than 30 mSv, depending on the radionuclide tracer used for the imaging procedure In conventional open chest CABG surgery, the patient's heart beat may be stopped while the circulation and oxygenation of blood is provided by an extracorporeal cardiopulmonary bypass using a heart-lung machine. This state is known as cardioplegic arrest. During surgery, two separate blood circulations are maintained. A systemic blood circulation delivers oxygenated blood to the body tissues. Cardioplegia fluids are delivered by a heart-lung machine, for example, that oxygenates the heart muscle, and that delivers nutrients and various drugs to the heart tissue, such as potassium to induce cardiac arrest. The result is a small circulation with a substantially small volume of blood oxygenating the heart and that is ready for delivering any substance to the heart vasculature, such as radiotracers used for imaging.

In each of these cases, imaging of small blood vessels in the heart, such as intramyocardial coronary arteries, may be useful for accessing the levels of cardiac dysfunction such as ischemia. However, many of the imaging techniques, as described above, used to detect the radiation from injected radiotracers may lack the imaging resolution needed for imaging these small blood vessels. Thus, these techniques may be incapable of determining if blood flow is improved in these small blood vessels, for example, so as to assess the effectiveness of the therapeutic treatments such as OPCABG and/or CABG.

SUMMARY OF THE INVENTION

There is thus provided, in accordance with an embodiment of the present invention, a gamma camera including: a detector array of a plurality of detector pixels, each detector pixel configured to generate a signal indicative of gamma or x-ray radiation incident on that detector pixel; a collimator array of a plurality of collimators, each collimator of the plurality of collimators configured to collimate the radiation onto a detector pixel of the plurality of detector pixels; an actuator configured to move the collimator array along an axis in one or a plurality of incremental movements, each incremental movement smaller than a lateral dimension of a detector pixel of the plurality of detector pixels along that axis; and a processor configured to obtain the signals generated by each detector pixel of the plurality of detector pixels and to generate image data with sub-pixel resolution from the sampled signals and a position of the collimator when each signal was generated.

Furthermore, in accordance with an embodiment of the present invention, a detector pixel of the plurality of detector pixels includes a cadmium-zinc-telluride (CZT) detector.

Furthermore, in accordance with an embodiment of the present invention, the gamma camera includes one or more imaging sensors, and the processor is configured to superimpose the image data on an image acquired by the one or more imaging sensors.

Furthermore, in accordance with an embodiment of the present invention, an imaging sensor of the one or more imaging sensors is selected from a group consisting of a complementary metal oxide semiconductor (CMOS) sensor, a charge coupled device (CCD) sensor, a near infrared sensor (NIR), and an ultrasound probe sensor.

Furthermore, in accordance with an embodiment of the present invention, the gamma camera includes a switch configured to turn on and off crosshair laser markers.

Furthermore, in accordance with an embodiment of the present invention, the actuator includes a motor.

Furthermore, in accordance with an embodiment of the present invention, the actuator is configured to move the collimator array while the detector array remains fixed.

Furthermore, in accordance with an embodiment of the present invention, the actuator is configured to move the collimator array together with the detector array.

Furthermore, in accordance with an embodiment of the present invention, the collimator array includes two collimator sub-arrays, and wherein the actuator is configured to separately move each of the two collimator sub-arrays.

Furthermore, in accordance with an embodiment of the present invention, the gamma camera includes a heart-lung machine to inject a radionuclide for generating the radiation into a cardioplegia blood circulation.

Furthermore, in accordance with an embodiment of the present invention, the gamma camera includes a disposable sterile cover.

There is further provided, in accordance with an embodiment of the present invention, a method for operation of a gamma camera, the method including: moving a collimator array of a plurality of collimators relative to a detector array of a plurality of detector pixels with one or a plurality of incremental movements, each incremental movement smaller than an than a lateral dimension of a detector pixel of the plurality of detector pixels along an axis of motion; using a processor, obtaining a signal from each detector pixel of the plurality of detector pixels, the signal indicative of gamma radiation incident on that detector pixel; and generating image data with sub-pixel resolution from the sampled signals and a position of the collimator when each signal was generated.

Furthermore, in accordance with an embodiment of the present invention, the method includes outputting the generated image data.

Furthermore, in accordance with an embodiment of the present invention, the method includes merging the image data with an image acquired by one or more imaging sensors.

Furthermore, in accordance with an embodiment of the present invention, an imaging sensor of the one or more imaging sensors is selected from a group consisting of a complementary metal oxide semiconductor (CMOS) sensor, a charge coupled device (CCD) sensor, a near infrared sensor (NIR), and an ultrasound probe sensor.

Furthermore, in accordance with an embodiment of the present invention, moving the collimator array includes operating a motor.

Furthermore, in accordance with an embodiment of the present invention, moving the collimator array includes moving the collimator array while the detector array remains fixed.

Furthermore, in accordance with an embodiment of the present invention, moving the collimator array includes moving the collimator array together with detector array.

Furthermore, in accordance with an embodiment of the present invention, the collimator array includes two collimator sub-arrays, and wherein moving the collimator array includes separately moving each of the two collimator sub-arrays.

Furthermore, in accordance with an embodiment of the present invention, the method includes operating a heart-lung machine to inject a radionuclide for generating the radiation into a cardioplegia blood circulation.

BRIEF DESCRIPTION OF THE DRAWINGS

In order for the present invention, to be better understood and for its practical applications to be appreciated, the following Figures are provided and referenced hereafter. It should be noted that the Figures are given as examples only and in no way limit the scope of the invention. Like components are denoted by like reference numerals.

FIG. 3A schematically illustrates components of the gamma camera shown in FIG. 1;

FIG. 3B schematically illustrates a two dimensional detector array of a detector unit of the gamma camera shown in FIG. 3A;

FIG. 3C schematically illustrates detection of collimated radiation by a detector pixel of the gamma camera shown in FIG. 1A when a collimator is centered on the detector pixel;

FIG. 3D schematically illustrates detection of collimated radiation by a detector pixel of the gamma camera shown in FIG. 1A when a collimator is not centered on the detector pixel;

DETAILED DESCRIPTION OF THE INVENTION

Figure 1:
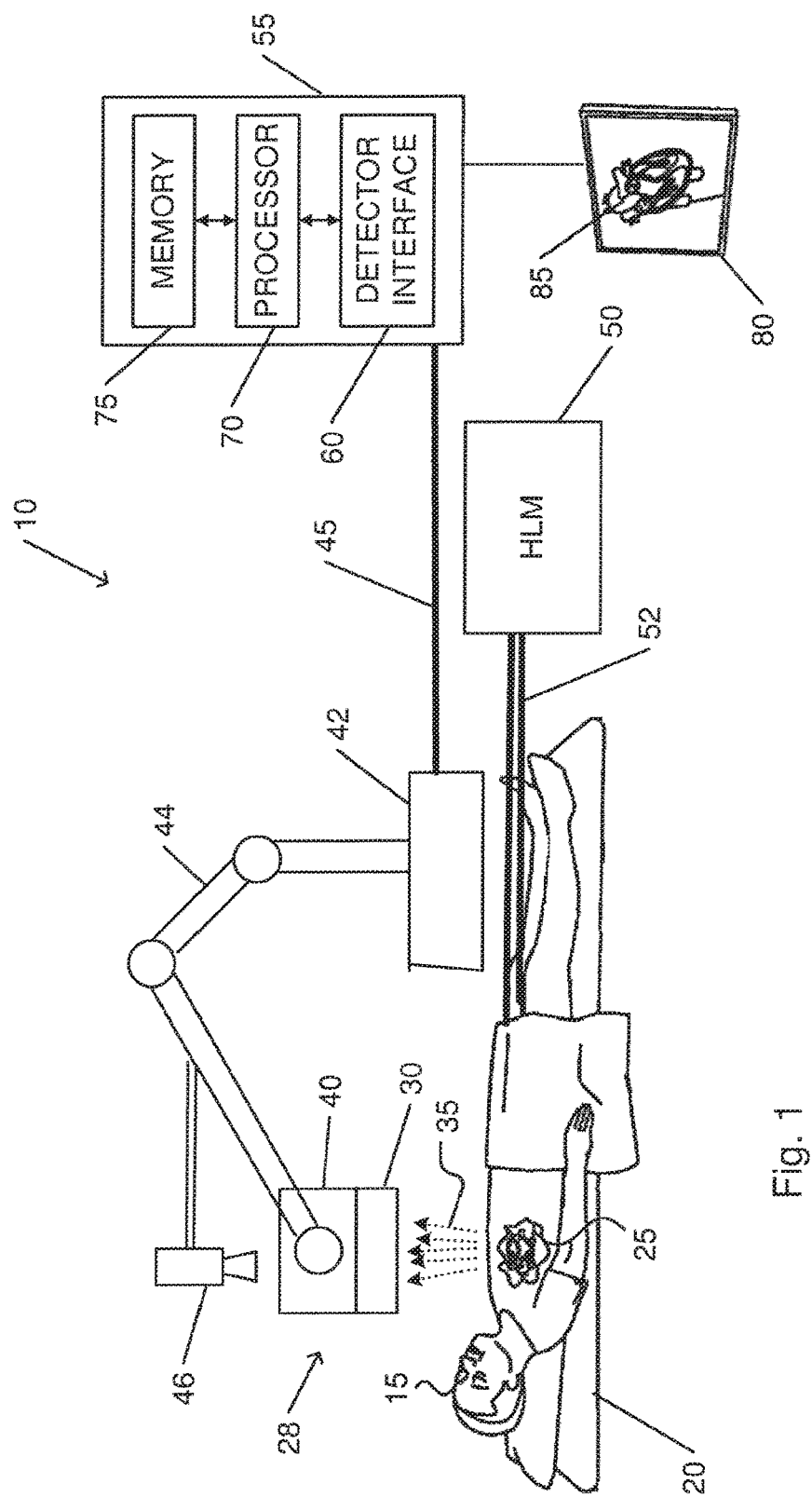
FIG. 1 schematically illustrates a system for improving imaging resolution of a gamma camera during intraoperative angiography, in accordance with some embodiments of the present invention.

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, use of the conjunction "or" as used herein is to be understood as inclusive (any or all of the stated options).

Some embodiments of the present invention described herein relate to a method and apparatus for real-time, improved resolution of intraoperative radioactive imaging of an organ of the body, such as the human heart. During a cardiac procedure, such as intraoperative angioplasty, the subject may be injected with radionuclides into the venous system of the subject which reaches the heart. The level of emission of radiation spatially is dependent upon the absorption of the radiation of the different tissue in the heart. Spatial detection of this emission may be used to image the heart using a gamma camera, for example. The term gamma camera as used herein may refer to any imaging device and/or sensor and/or camera capable of detecting gamma ray radiation or x-ray radiation (e.g., at photon energies that approach, or border on, the spectral range of gamma radiation).

In some embodiments of the present invention, a gamma camera may be positioned over the heart during surgery. The gamma camera may include a collimator array of a plurality of collimators. The collimators may collimate gamma radiation that is emitted from the radionuclides in the heart tissue onto an array of pixels of a detector. The radiation impinging on the detector array may form a set of spatial image data. Each collimator directs gamma radiation photons that are incident on an entrance aperture of the collimator within a predetermined range of angles out of an exit aperture and onto a corresponding pixel of the pixelated detector. Each collimator in the collimator array collimates the incident radiation onto an active area of the corresponding pixel (the active area being a region of each pixel where incident radiation may be converted into an output signal). Active regions of adjacent pixels may be separated by regions that are inactive (e.g., where incident radiation is not converted to an output signal). The area of the exit aperture of each collimator, and thus of the collimated radiation that impinges on the corresponding pixel of the pixel array, is typically smaller than the active area of the pixel.

In the absence of such a collimator, the resolution in the image data would be limited by the size of the active area. Thus, a relatively large active area would yield relatively low resolution (e.g., since radiation that is incident on all parts of the active area would contribute to a single output signal). On the other hand, collimation that limits incident radiation to a fraction of the area of the pixel, together with knowledge of the position of the collimator relative to the pixel, could enable distinguishing radiation that is incident on different parts of the active area. Thus, the resolution may be the resolution that would be attainable if the size of the active area were that of the entrance aperture of the collimator.

The collimator array or the detector pixel array may be coupled to an actuator which may induce one or a plurality of incremental movements in the collimator array, the detector pixel array, or both. These incremental movements cause a relative motion between collimated radiation entering the plurality of collimators and a pixel of the detector pixel array. Moving the radiation spot (herein referring to a region that is irradiated by radiation that exits the exit aperture of the collimator) over the active area of the pixel enables the creation of a plurality of images with sub-pixel translation. The resulting image data, when processed using super resolution methods, may have sub-pixel resolution.

For example, in coronary artery detection and assessment of a graft, such as a cardiac artery bypass graft (CABG), the improved resolution gamma camera may be used to capture real-time images, to enable detection of small hidden arteries such as intramyocardial arteries, and to assess the real-time effectiveness of the therapeutic grafting procedure (e.g., the effectiveness of blood flow in the affected blood vessels) to alleviate cardiac dysfunction. It should be understood that although the embodiments presented herein mainly relate to enhancing resolution of cardiac images in intraoperative angiography, the device and methods described herein may also be used to image other body organs or tissues.

FIG. 1 schematically illustrates a system 10 for improving imaging resolution of a gamma camera 28 during intraoperative angiography, in accordance with some embodiments of the present invention. A subject 15 lying on a surface 20 (e.g., a bed, gurney, or other surface) may undergo an open heart procedure, for example, exposing a heart 25. A user of system 10 such as a physician, surgeon, nurse, technician, or other health care professional may deliver radionuclides through a tube 52 to the blood system of subject 10. Tube 52 may represent a system of two or more component tubes. For example, one component tube may deliver radionuclides to subject 15, while another may collect radionuclides from subject 15 (e.g., directable back to subject 15, to a waste receptacle, or elsewhere).

Radiation 35 emitted by the radionuclides in the region of heart 25 may be collected with gamma camera 28. Gamma camera 28 may include a collimator unit 30 and a detector unit 40. Radiation 35 may be used to image heart 25. Gamma camera 28 may be suspended above subject 15 on an arm 44 attached to a base 42 (e.g., in the form of a stationary base or cabinet attached to a floor, wall, or ceiling, or in the form of a wheeled or portable cart, stand, or other type of base) positioned near subject 15 by the user. Alternatively or in addition, gamma camera 28, arm 44, or both may be attached to a wall or ceiling, or may be handheld.

Radiation 35 collected by gamma camera 28 may be converted to electrical signals in detector unit 40. The resulting electrical signals may be relayed via a cable 45 to an image processing unit 55. Image processing unit 55 may include a detector interface 60 for receiving the electrical signals relayed from gamma camera 28 over cable 45, a processor 70, and a memory 75. Image processing unit 55 (e.g., processor 70 of image processing unit 55) may be used to process the electrical signals from gamma camera 28 and may be used to generate image data, e.g., of heart 25, as shown in the example shown in FIG. 1. The user may view a real time image 85 of heart 25 (or of another organ) from the processed image data on a display 80.

One or more imaging sensors 46, such as a video camera, infrared camera, or other type of sensor, may be attached to arm 44 or otherwise mounted or held. Imaging sensors 46 may include one or more imaging or other sensors, such as a complementary metal oxide semiconductor (CMOS) sensor, a charge coupled device (CCD) sensor, a near infrared sensor (NIR), an ultrasound probe sensor, or another type of sensor. Although imaging sensors 46 are shown attached to arm 44, the one or more imaging sensors 46 may be placed in another position.

Secondary image data acquired from imaging sensors 46 may be superimposed with the image data acquired by gamma camera 28 (e.g., a heart 25, in the example shown in FIG. 1). Processor 70 may be used to register the coordinate system of the image data of gamma camera 28 with the respective coordinate systems of the one or more imaging sensors 46. The secondary image data from imaging sensors 46 may then be used for image enhancement of the image data generated by gamma camera 28 to form real time image 85 of heart 25 on display 80.

Processor 70 may include one or more, processors, or one or more processing units, e.g. of one or more computers. Processor 70 may be configured to operate in accordance with programmed instructions stored in memory 18. Processor 70 may be configured to execute an application for analyzing image data acquired by gamma camera 28 and to control the functionality of gamma camera 28.

Processor 70 may be configured to communicate with output device, such as display 80. For example, display 80 may include a computer monitor or screen. Processor 70 may communicate with a screen of output device 80 to display real time images of heart 25, for example, or any other organ or tissue being imaged as captured from image data from gamma camera 28 or other visible output. In another example, an output device may include a printer, display panel, speaker, or another device capable of producing visible, audible, or tactile output.

Processor 70 may be configured to communicate with an input device (not shown in FIG. 1). For example, input device may include one or more of a keyboard, keypad, or pointing device for enabling a user to inputting data or instructions for operation of processor 80.

Processor 70 may be configured to communicate with memory 75. Memory 75 may include one or more volatile or nonvolatile, permanent or removable, memory devices or data storage devices. Memory 75 may be utilized to store, for example, programmed instructions for operation of processor 70, data or parameters for use by processor 70 during operation, or results of operation of processor 70

In operation, processor 70 may execute a method for controlling gamma camera 28 and for processing image data acquired from gamma camera 28.

Components of image processing unit 55 or of system 10 may include an article such as a computer or processor readable medium, or a computer or processor non-transitory storage medium, such as for example a memory, a disk drive, or a USB flash memory, encoding, including or storing instructions, e.g., computer-executable instructions, which when executed by a processor or controller, carry out methods disclosed herein.

In some cases, the radionuclides may be delivered directly (e.g., off-pump) to subject 15 via tube 52 without the need for cardioplegic arrest.

In some cases, a separate (from systemic blood circulation that circulated to the body of subject 15) cardioplegia blood circulation is created by a heart-lung machine (HLM) 50. The cardioplegia blood circulation may be applied through tube 52 to the muscles of heart 25 using the common drug delivery mechanism for the cardioplegia. Tube 52 may also be used to deliver radionuclides to the coronary arteries through the cardioplegia blood circulation (and to return blood and radionuclides to HLM 50). In this manner, the radionuclides are delivered only to the coronary blood vessels using the separate blood circulation to heart 25 that is maintained by HLM 50 for the purpose of delivering drugs for inducing cardiac arrest via tube 52. This method is suitable to work in conjunction with any modern HLM 50.

The separate blood circulation to the heart has a very small volume relative to systemic circulation. Therefore, only very small volumes (e.g., relative to delivery via systemic circulation) of delivered radionuclides may generate a high concentration of radionuclides in the cardioplegia blood circulation. Thus, high quality images may be acquired while exposing the body to a relatively low dose of total body radiation. A minimal radiation dose may be maintained by delivering radionuclides via cardioplegia blood circulation using a radiation protected delivery system, or otherwise generating a small blood circulation that is separate from the systemic circulation.

Radionuclide tracers, such as Technetium-99m labeled albumin and similar tracers, for example, introduced and returned, through component tubes of tube 52 do not penetrate the surrounding tissues and remain in the circulating blood. In some cases, the radionuclides may be delivered antegrade through the aorta and collected from the coronary sinus vein or the chest cavity. The radionuclides may also be delivered retrograde to the coronary sinus and collected from the aorta or the chest cavity. In other cases, the radionuclides may be delivered and collected via a radiation absorbing delivery system including an automated syringe and tubing system. The radionuclides may then be collected to a radiation shielded bin or container in order to prevent or reduce stray radiation.

Gamma camera 28 may be designed for intraoperative use by a user (e.g., handheld, suspended, or otherwise) to acquire radiation data from gamma radiation emitted from a radiation source, e.g. radionuclides absorbed in or transported by biological tissue. In some cases, detector unit 40 may include a solid state detector, for example, that converts radiation to electricity by direct conversion. In some cases, gamma camera 28 may feature an integrated on-device monitor or other monitor. Gamma camera 28 may include a disposable cover for placement in contact with the patient so as to provide and maintain sterile conditions during the medical procedure. (In some cases, processing of acquired data may include correction for movement of a handheld gamma camera 28.)

In some cases, processor 70 may be used to a fuse data from one or more imaging sensors 46, such as a visible (VIS) spectral sensor, a near infrared (NIR) sensor, an ultrasound probe, or one or more other sensors. The data from imaging sensors 46 may be used for optimizing the image from gamma camera 28, and for displaying a fused image in which the gamma image is superimposed on an image that is acquired using one or more imaging sensors 46 (e.g., image of heart 85). The fused image may assist in interpretation of the gamma image.

Intramyocardial coronary arteries that cannot be located with precision during conventional CABG surgery, e.g., due to overlying with muscle tissue (intramyocardial coronary arteries), could increase the risk to a patient during surgery when an arterial bypass is needed. Increased resolution data images of the hidden arteries using system 10 may be used to detect the location of the small intramyocardial coronary arteries, for example.

System 10 may also be used to intraoperatively assess grafts by verification of the flow of blood through a connected bypass graft. Radionuclides may be delivered to the grafted artery so as verify the flow of blood carrying the radionuclides in the bypass and in subsequent arteries, myocardium, and the venous system.

Figure 2A:
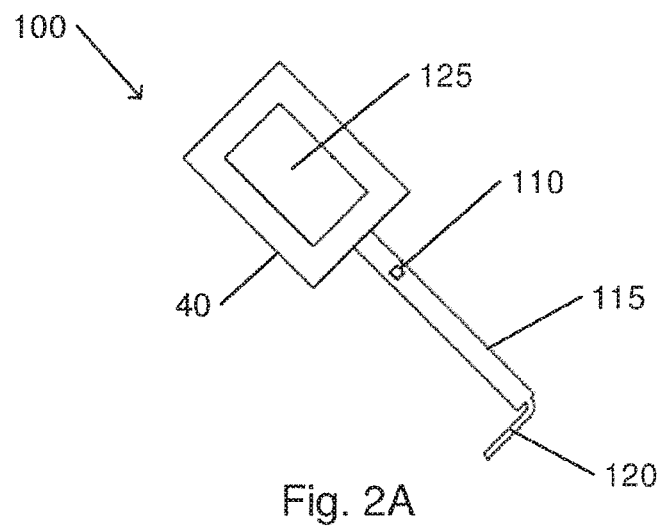
FIG. 2A schematically illustrates a top view of a compact gamma camera, in accordance with some embodiments of the present invention.

FIG. 2A schematically illustrates a top view of a compact gamma camera, in accordance with an embodiment of the present invention.

Figure 2B:
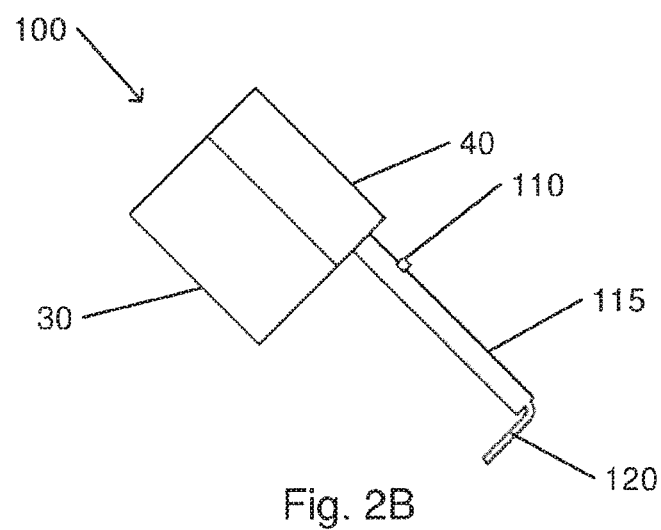
FIG. 2B schematically illustrates a side view of a compact gamma camera, in accordance with some embodiments of the present invention.

FIG. 2B schematically illustrates a side view of the compact gamma camera shown in FIG. 2A.

In some cases, compact gamma camera 100 may be handheld. Compact gamma camera 100 may include a handle 115, detector unit 40 (e.g., with solid state detectors), and collimator unit 30. Thus, compact gamma camera 100 may be manipulated so as to detect photons that are emitted from the radionuclides from the tissue to be imaged (e.g., heart 25) in different directions, For example, manipulation of compact gamma camera 100 may enable acquisition of both anterior and posterior views of the tissue to be imaged (e.g., heart 25). A display panel 125 may display images of the acquired data. The body of compact gamma camera 100 (as well as the body of gamma camera 28 of FIG. 1) may be covered by a replaceable sterile cover (not shown). Handle 115 may include a control 110 (e.g., a button or other type of user-operable control) which may be used to turn on or off crosshair laser markers that are projected onto the target organ and/or tissue (e.g., heart 25, or heart muscle, for example). The crosshairs may indicate the object (e.g., heart 25 or other organ) that is being imaged, and may enable the user to manipulate compact gamma camera 100 to a desired position and orientation.

In some cases, compact gamma camera 100 may include a retractable cable 120 which may be coupled to a computer (e.g., image processing unit 55) that accumulates and processes acquired data and reconstructed images. In some cases, the compact gamma camera 100 may include a built-in image processing unit which may include some or all of the functionality of image processing unit 55 in system 10.

FIG. 3A schematically illustrates components of the gamma camera shown in FIG. 1.

Detector unit 40 of gamma camera 28 may include, for example, a two-dimensional array of a plurality of detector pixels 155. (For clarity, only a linear array of detector pixels 155 is shown in FIG. 3.)

FIG. 3B schematically illustrates a two dimensional detector array of a detector unit of the gamma camera shown in FIG. 3A. Detector array 205 of a detector unit 40 includes a two-dimensional array of detector pixels 155. Although a uniform rectangular array of rectangular detector pixels is shown for clarity, each detector pixel may have another form (e.g., circular, oval, polygonal, or other form), and the array of detector pixels may have another form (e.g., staggered rows, diagonal rows, circular pattern, or another pattern).

Collimator unit 30 of gamma camera 28 includes collimator array 151 of a plurality of collimators 152. Each collimator 152 may be characterized by a collimation cross-section of its collimator aperture 150 (e.g., by aperture area). Collimator array 151 may be aligned with the array of detection pixels 155. An actuator 160 may be coupled to linear collimator array 151 so as to move collimator array 151 relative to the array of detector pixels 155, e.g., with collimator movement 154. The movements of actuator 160 may be controlled by processor 70. Thus, processor 70 may be used to synchronize the acquisition of the image data from detector unit 40 with movement of collimator array 151. Although movement 154 is shown in one dimension for clarity, actuator 160 may typically move collimator array 151 in two dimensions.

Actuator 160 may include a motor, such as an electric motor, or another type of actuator. Actuator 160 may be located within collimator unit 30 or may be external to collimator unit 30. Actuator 160 may be operated to effect relative translation between detector unit 40 and collimator unit 30.

In some cases, collimator array 151 and detector unit 40 may be configured to move together. For example, collimator array 151 and detector unit 40 may be mechanically connected to one another, such that actuator 160 moves both collimator array 151 and detector unit 40. In another example, actuator 160 (e.g., including a single actuator, two or more coordinated actuators, or otherwise) may be configured to move collimator array 151 and detector unit 40 in tandem. Moving collimator array 151 and detector unit 40 together in sub-pixels steps may enable sub-pixel sampling of gamma radiation.

FIG. 3C schematically illustrates detection of collimated radiation by a detector pixel of the gamma camera shown in FIG. 1A when a collimator is centered on the detector pixel.

For example, each detector further illustrates how incremental movements of collimators 152 relative to detector pixels 155 improve resolution. Each detector pixel 155 includes an active detection area 167. Gamma radiation that is incident on active detection area 167 may be converted to an electrical signal. In some cases, active detection area 167 of a detector pixel 155 may be surrounded (e.g., between active detection area 167 and outer edges of detector pixel 155) by an inactive region where incident radiation is not converted, or is not converted efficiently, to an electrical signal.

Radiation 35 that is incident on entrance aperture 150a of collimator aperture 150 in a direction that is approximately parallel to a longitudinal axis of collimator aperture 150 may exit from collimator aperture 150 exit through exit aperture 150b. Radiation that is not incident on entrance aperture 150a, or that is incident at an angle that is greater than a collimation angle of collimator 152 (the collimation angle being determined in part by the sizes of entrance aperture 150a and of exit aperture 150b, the length of collimator aperture 150, and on the interaction between walls of collimator 152 and the radiation) may be absorbed or scattered by the walls of collimator 152 that surround collimator aperture 150. Thus, radiation that is incident on collimator unit 30 may be collimated. The collimated radiation that exits from exit aperture 150b may impinge on a radiation spot on a detector pixel 155. The size and shape of the radiation spot may depend on factors that include the size of exit aperture 150b, the collimation angle, and the distance between exit aperture 150b and detector pixel 155.

When collimator array 30 is aligned to be centered on detector unit 40 (e.g., such that a central axis of each collimator aperture 150 of each collimator 152 approximately intersects a center of active detection area 167 of a corresponding detector pixel 155), radiation 35 that is collimated by passing through collimator aperture 150 of collimator 152 may impinge on a radiation spot 170a at the center of active detection area 167 (as shown in FIG. 3C). When radiation spot 170a is smaller than active detection area 167, a portion of active detection area 167 may not be illuminated.

Translation of collimator array 151 relative to detector unit 40 may cause a corresponding translation of the radiation spot relative to active detection area 167, e.g., to an off-center location on active detection area 167.

FIG. 3D schematically illustrates detection of collimated radiation by a detector pixel of the gamma camera shown in FIG. 1A when a collimator is not centered on the detector pixel.

In this case, collimator aperture 150 has been translated relative to active detection area 167 of detector pixel 155. Therefore, a different subset of radiation 35 enters entrance aperture 150a of collimator aperture 150 to be collimated onto detector pixel 155. Also as a result, translated radiation spot 170b is not centered on active detection area 167. A controller or processor of system 10 may be configured to monitor the relative translation and to associate each electric signal that is generated by detector pixel 155 with the relative location of collimator aperture 150 to active detection area 167.

In the example shown, radiation spot 170a and translated radiation spot 170b are shown as rectangular, e.g., as resulting from a rectangular cross section of collimator aperture 150. In other examples, a radiation spot may be circular, oval, polygonal, or have another shape.

Actuator 160 may be operated to translate collimator aperture 150 to a plurality of predetermined locations relative to active detection area 167. Thus, moving the collimators with incremental movements can be used to irradiate slightly different (subpixel difference) parts of active detector area 167 with different components (e.g., rays) of radiation 35. By recording the expected position of the resulting translated radiation spot 170b in association with the signal that is generated by detector pixel 155 at each position, subpixel resolution may be achieved.

In the example shown in FIG. 3D, part of translated radiation spot 170b extends beyond the boundaries of active detection area 167. (In some cases, the area of active detection area 167 is equal to, or almost equal, to that of detector pixel 155.) Therefore, the irradiation in those parts of translated radiation spot 170b may not contribute to the signal that is generated by detector pixel 155. In processing the signals to form an image, the signal that is generated by detector pixel 155 may be adjusted accordingly. For example, if a pre-calculated fraction of translated radiation spot 170b lies within the boundaries of active detection area 167, the resulting signal may be adjusted by multiplication of a factor that is the inverse of that fraction.

In some cases, a calibration process may be executed in order to calculate the relative signals that are generated by each detector pixel 155 for each position of collimator array 151. For example, during the calibration process, gamma camera 28 may be irradiated by a spatially uniform source of gamma radiation as collimator array 151 is translated relative to detector unit 40. Alternatively or in addition, a constant source of gamma radiation may successively illuminate different collimators 152, or different groups of neighboring collimators 152.

In some cases, detector unit 40 of gamma camera 28 may include one or more solid state detectors. Each detector pixel 155 of detector unit 40 may be formed from a semiconductor material, such as cadmium-zinc-telluride (CZT) or CdZnTe-based detector materials. These materials may transform the high energy gamma photons that are emitted by the radionuclides to electrical signals. The electrical signals may be processed to generate the image data. This set of electrical signals, each electrical signal of the set corresponding to a detector pixel 155 of detector unit 40, may be sampled. For example, sampling using an application specific integrated circuit (ASIC) board may measure the readings over a specific integration period to obtain (e.g., after processing) a set of measurements of the radionuclide concentrations at the spatial points of measurement in heart 25, for example.

For example, detector unit 40 may include an array of 16×16, or 256, detector pixels 155. In some cases, the size of the array may range from about 25 mm×25 mm to about 40 mm×40 mm. Detector unit 40 may include one or more of a field programmable grid array (FPGA) integrated circuit, an electronically erasable programmable read-only memory (EEPROM), analog-to-digital converters, a heat sink, and a base current (Id) injector. Collimator unit 30 of collimators 152 may be placed between the detector unit 40 and subject 15 (e.g., the tissue of subject 15 that is being examined) to limit the photons that arrive to each detector pixel 155 to those that are incident on collimator unit 30 within a predetermined collimation angle. The collimation may thus provide better directionality to gamma camera 28.

In one example, each detector pixel 155 may include a CZT or other type of detector (or a region of a detector) with an area of 2.46 mm×2.46 mm with an active detection area 167. Radiation spot 170a or translated radiation spot 170b may have a spot size of 1.26 mm×1.26 mm, in some cases as small as 0.5 mm×0.5 mm. In this case, the area of radiation spot 170a or translated radiation spot 170b may be substantially smaller (e.g., ranging from ¼ to ¹⁄₂₅) than the area of detector pixel 155. Therefore, in the resulting image, the resolution may be greater (e.g., ×25, with 25 separate signal acquisitions) than the resolution that would be achieved without the translation of translated radiation spot 170b.

For example, each collimator 152 may include walls made of a material that absorbs gamma radiation, such as tungsten, lead, or another gamma absorber. Typically, the collimator walls are perpendicular to the sensor. The wall thickness may be about 0.6 mm, or another thickness sufficient to provide a required or desired attenuation. For example, if the center-to-center distance (pitch) between adjacent collimators 152 is about 2.46 mm, the width of radiation spot 170a or translated radiation spot 170b may be about 1.86 mm.

Actuator 160 may be operated to move collimator array 151 with a predetermined pattern of movements.

Figure 4A:
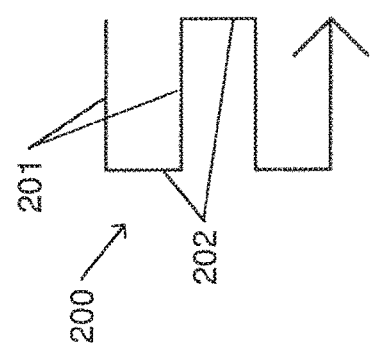
FIG. 4A schematically illustrates a plurality of incremental movements by an actuator for moving collimators, in accordance with some embodiments of the present invention.

FIG. 4A schematically illustrates a pattern of incremental movements of the collimator shown in FIG. 3A.

Actuator 160 may effect collimator movement 154 in the form of movement pattern 200 in two dimensions (substantially parallel to the plane of detector pixels 155 and of exit apertures 150b. For example, movement pattern 200 may include incremental movement steps 201 and 202 in two orthogonal dimensions. Alternatively or in addition to orthogonal movement steps, a movement pattern may include movement steps in other directions (e.g., within a single plane).

Each incremental movement step 201 or 202 may typically be smaller than a lateral dimension of pixel 155, active detection area 167, or of translated radiation spot 170b in the direction of that incremental movement step 201 or 202 (e.g., may be described as a sub-pixel step or movement). For example, in the case of a rectangular radiation spot (e.g., approximately equal in size to a length and width of exit aperture 150b of collimator 152), an incremental movement step 201 or 202 parallel to the length or width of translated radiation spot 170b may be smaller than the length or width, respectively.

Moving collimators 152 with movement pattern 200 may cause different regions of radiation 35 (e.g., offset from one another by approximately the size of incremental movement step 201 or 202) to be sampled (e.g., in a raster pattern). Thus, resolution of sampling of radiation 35, and thus of the imaged organ of subject 15, may be increased over sampling in the absence of collimator movement 154 along movement pattern 200.

When movement along movement pattern 200 is complete, further collimator movement 154 may reverse the direction of movement pattern 200, or may continue otherwise (e.g., in the example show, begin with a movement that is opposite to incremental movement step 202, directly return to the starting point of movement pattern 200, or otherwise continue movement).

In some cases, collimator array 151 and detector unit 40 may be configured to move together. For example, collimator array 151 and detector unit 40 may be mechanically connected to one another. In another example, actuator 160 (e.g., including a single actuator, coordinated actuators, or otherwise) may be configured to move collimator array 151 and detector unit 40 in tandem.

Figure 4B:
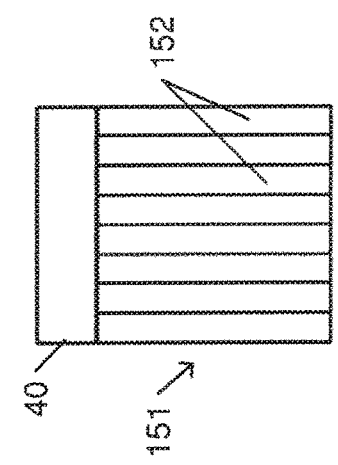
FIG. 4B schematically illustrates a pixel array in a pixelated detector unit, in accordance with some embodiments of the present invention.

FIG. 4B schematically illustrates a single collimator array and a detector unit of the gamma camera shown in FIG. 3A.

As shown, collimator array 151 of single collimators 152 is in a first position relative to detector unit 40.

Figure 4C:
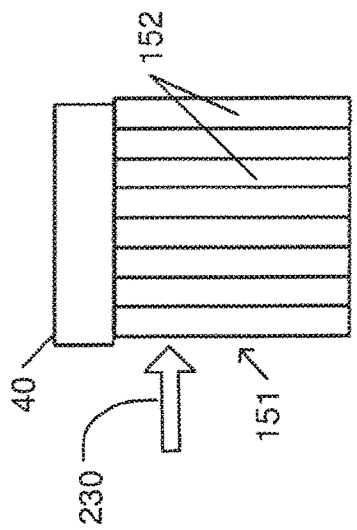
FIG. 4C schematically illustrates a collimator array of collimators in a first position relative to a pixelated detector unit, in accordance with some embodiments of the present invention.

FIG. 4C schematically illustrates translation of the single collimator array shown in FIG. 4B.

In FIG. 4C, collimator array 151 has been displaced by displacement 230 to a second position relative to detector unit 40. Actuator 160 may move collimators 152 in the direction of displacement 230. As a result, the portion of radiation 35 that is collimated by each collimator 152 is displaced relative to the portion that is collimated in the position shown in FIG. 4B (e.g., approximately by displacement 230).

In some cases, a collimator unit may include a double array of collimators. For example, a proximal array of collimators array may abut detector unit 40 (as shown, e.g., in FIG. 4B with regard to collimator array 151 and detector unit 40). A distal array of collimators may abut a distal side of the proximal collimator array. For example, the distal collimator array may be permanently displaced relative to the proximal collimator array. The displacement may be such that the aperture of each collimator of the distal array partially overlaps the aperture of a single collimator of the proximal array. In this case, the effective aperture of each collimator pair (of one proximal collimator and a corresponding distal collimator) may be approximately equal to the area of the overlap, and less than the area of either aperture by itself. Therefore, actuating the double array to manipulate both collimator arrays in tandem may scan the effective aperture across radiation 35. Alternatively or in addition, the distal and proximal collimator arrays may be separately manipulated (e.g., by separate actuators) to be translated relative to one another (e.g., in parallel planes) and relative to detector unit 40.

Such a double array of collimators may enable increasing resolution over a single collimator array without reducing the size of the collimator apertures. In this manner, finer resolution may be achieved without increasing the precision (e.g., entailing increased expense) of the formation of each collimator. In some cases, the apertures of collimators of the distal collimator array may be smaller than the apertures of the collimators of the proximal collimator array.

Figure 4D:
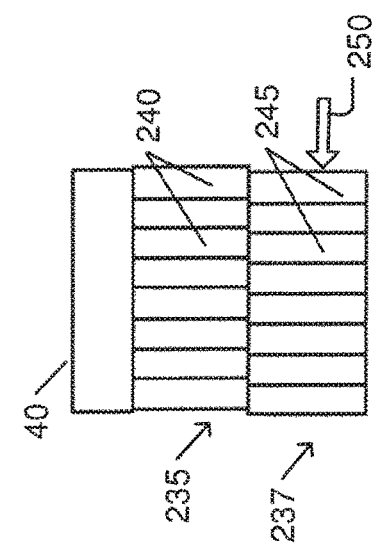
FIG. 4D schematically illustrates a collimator array of collimators in a second position relative to a pixelated detector unit, in accordance with some embodiments of the present invention.

FIG. 4D schematically illustrates a double array of collimators, in accordance with an embodiment of the present invention.

Proximal collimator array 235 of proximal collimators 240 abuts detector unit 40. Distal collimator array 237 of distal collimators 245 abuts the distal end of proximal collimator array 235. Distal collimator array 237 is laterally displaced FIG. 4E schematically illustrates a translation of the double array of collimators shown in FIG. 4D.

Figure 4E:
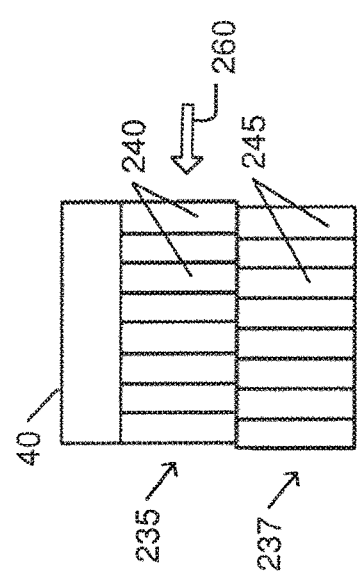
FIG. 4E schematically illustrates a side view of two collimator sub-arrays, in accordance with some embodiments of the present invention.

In FIG. 4E, proximal collimator array 235 has been displaced relative to its position in FIG. 4D by displacement 260. Similarly, distal collimator array 237 has been displaced in tandem relative to its position in FIG. 4D by displacement 260.

The manipulation of proximal collimator array 235 and of distal collimator array 237 may scan a smaller radiation spot across active detection area 167 of each detector pixel 155 than would be achieved by a single collimator array. The smaller radiation spot corresponds to sampling of a smaller region of radiation 35, and thus increased resolution in sampling radiation 35 (and in imaging a part of subject 15).

Figure 4F:
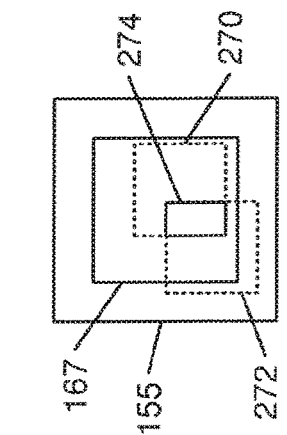
FIG. 4F schematically illustrates collimation by the two collimator sub-arrays shown in FIG. 4E.

FIG. 4F schematically illustrates a radiation spot that is produced by the double collimator array shown in FIG. 4d.

In the example shown, proximal collimator radiation spot 270 represents the radiation spot that would be formed by a proximal collimator 240 in the absence of distal collimator array 237. Similarly, distal collimator radiation spot 272 represents the radiation spot that would be formed by a distal collimator 245 in the absence of proximal collimator array 235. (In some cases, distal collimator radiation spot 272 may be larger than proximal collimator radiation spot 270 due the increased distance between distal collimator 245 and detector pixel 155.) Double collimator radiation spot 274, representing the region of active detection area 167 that is actually irradiated after the double collimation, is formed where proximal collimator radiation spot 270 overlaps distal collimator radiation spot 272.

By translating proximal collimator array 235 and distal collimator array 237 in tandem, double collimator radiation spot 274 may be scanned across active detection area 167. Equivalently, a sampled region of radiation 35 that corresponds to double collimator radiation spot 274 may be scanned across radiation 35. Separate manipulation of proximal collimator array 235 and of distal collimator array 237 (e.g., displacing either or both) may adjust the size of double collimator radiation spot 274, as well as its position on active detection area 167.

Processor 70 of image processing unit 55 may be configured to operate in accordance with instruction saved in memory 75 to execute a method for subpixel resolution image acquisition, in accordance with an embodiment of the present invention.

Figure 5:
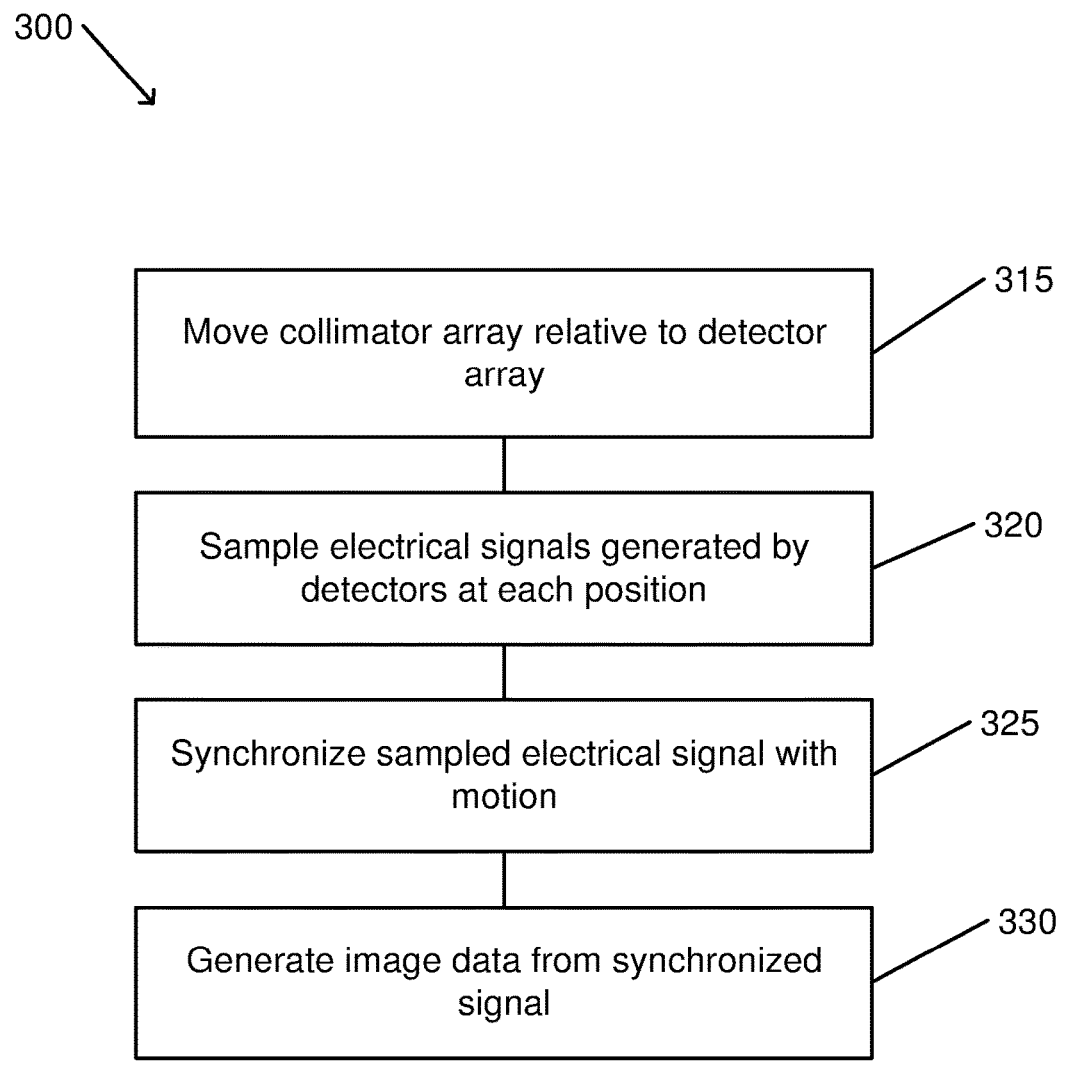
FIG. 5 is a flowchart depicting a method for improving resolution of image data in a gamma camera, in accordance with some embodiments of the present invention.

FIG. 5 is a flowchart depicting a method 300 for subpixel resolution image acquisition with a gamma camera, in accordance with an embodiment of the present invention.

It should be understood with respect to any flowchart referenced herein that the division of the illustrated method into discrete operations represented by blocks of the flowchart has been selected for convenience and clarity only. Alternative division of the illustrated method into discrete operations is possible with equivalent results. Such alternative division of the illustrated method into discrete operations should be understood as representing other embodiments of the illustrated method.

Similarly, it should be understood that, unless indicated otherwise, the illustrated order of execution of the operations represented by blocks of any flowchart referenced herein has been selected for convenience and clarity only. Operations of the illustrated method may be executed in an alternative order, or concurrently, with equivalent results. Such reordering of operations of the illustrated method should be understood as representing other embodiments of the illustrated method.

Method 300 may be executed by processor 70 of system 10 for subpixel resolution image acquisition during intraoperative angiography. The angiography may include injecting a radionuclide into one or more blood vessels of a subject (e.g., of a heart 25). The injection may include using HLM 50 to circulate blood with the radionuclide through a blood vessel of heart 25.

Method 300 includes operating an actuator 160 to move collimator array 151 relative to detector array 205 of a plurality of detector pixels 155 (block 315). The movement may include a movement pattern 200 of one or a plurality of incremental movement steps 201 of 202. Each movement may be smaller than a dimension of the active detection area 167 in a direction parallel to the movement. Each movement may be smaller than a length of an exit aperture 150b of a collimator 152 (or of a radiation spot 170a) in a direction parallel to the movement. In some cases, each incremental movement step 201 or 202 may be recorded together with a time stamp. In some cases, a starting time of movement pattern 200 may be recorded, with each incremental movement step 201 or 202 occurring at a predetermined time after the start of movement pattern 200. The collimator array may include a single collimator array, or a double collimator array including a proximal collimator array 235 and a distal collimator array 237.

At each position, an electric signal that is generated by each detector pixel 155 is sampled (block 320). For example, each sampled electrical signal, together with a time stamp, may be saved in memory 75.

The sampled electrical signals may be synchronized with the movement of collimator array 151 (block 325). For example, a known time of each sampled signal may be associated with a position of a collimator array 151 based on known sampling times and known times of each incremental movement step 201 or 202.

An image may be generated based on the synchronized data (block 330). A pixel of the image may be generated at a position that corresponds to each position of a translated radiation spot 170b on an active detection area 167 of each detector pixel 155. Thus, the resulting subpixel resolution of the image may be greater than the resolution that would be obtained without movement of collimator array 151. For example, the image may be of an organ of a subject 15.

In some embodiments of the present data, processor 70 may be used to reconstruct the image data generated from detector unit 40 using digital signal processing (DSP) with image quality algorithms for generating subpixel resolution image data. In some cases, a real-time image 85 of heart 25 may be generated by merging the subpixel resolution image data from gamma camera 28 with image data from one or more imaging sensors 46 (e.g., VIS sensor, NIR sensor, ultrasound sensor, or another sensor). Real time image 85 of heart 25 for output on display 80 in the operating room to provide real time angiographic imaging of the needed blood vessels.

In some embodiments of the present invention, processor 70 may generate a spatial transformation matrix between the gamma image and the auxiliary sensor (e.g., VIS, NIR, and ULS). Before the injection of the radionuclide, the geometrical distortion of the projected image onto detector unit 40 (the distortion arises from projecting a three-dimensional object to a two-dimensional image) may be obtained by calculating the distance from the heart to gamma camera 28, and the voxel that is derived from the positioning of gamma camera 28. Two LED cross-like beams may be projected on a diagonal line of the field of view. The reflection of the beam may be analyzed to determine the size of the voxel and the distance of the object from the device. In order to correlate between the VIS data and the gamma sensor, registering the coordinate systems of the VIS image data and data from gamma camera 28, the pixel mapping of gamma sensor 28 may be calibrated with the pixel map of the VIS sensor.

In some embodiments of the present invention, processor 70 may generate a high resolution image from a plurality of low resolution images, using super resolution processing methods. For example, processor 70 may solve the linear set problem $y = A \cdot x + N$, where y represents a low resolution image created by performing a measurement A on an object x, with the addition of noise N. This equation can be solved by minimizing a penalty function. For example, minimizing a penalty function may include applying a least squares technique that minimizes the norm of the residuals and reduces the problems that arise from noise added during the measurement.

Different embodiments are disclosed herein. Features of certain embodiments may be combined with features of other embodiments; thus certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A gamma camera comprising:
   a detector array of a plurality of detector pixels, each detector pixel configured to generate a signal indicative of gamma or x-ray radiation incident on that detector pixel;
   a collimator array of a plurality of collimators, each collimator of said plurality of collimators configured to collimate a sampled portion of the radiation onto a detector pixel of said plurality of detector pixels;
   an actuator configured to move the collimator array relative to the detector array along an axis in one or a plurality of incremental movements, each incremental movement being smaller than a lateral dimension of a detector pixel of said plurality of detector pixels along that axis so as to cause each collimator of the plurality of collimators to sample a different portion of the radiation; and
   a processor configured to obtain the signals generated by each detector pixel of said plurality of detector pixels and to generate image data with sub-pixel resolution from the signals and a position of the collimator when each signal was generated.

2. The gamma camera of claim 1, wherein a detector pixel of said plurality of detector pixels comprises a cadmium-zinc-telluride (CZT) detector.

3. The gamma camera of claim 1, further comprising one or more imaging sensors, wherein the processor is configured to superimpose the image data on an image acquired by said one or more imaging sensors.

4. The gamma camera of claim 3, wherein an imaging sensor of said one or more imaging sensors is selected from a group consisting of a complementary metal oxide semiconductor (CMOS) sensor, a charge coupled device (CCD) sensor, a near infrared sensor (NIR), and an ultrasound probe sensor.

5. The gamma camera according to claim 1, further comprising a switch configured to turn on and off crosshair laser markers.

6. The gamma camera of claim 1, wherein the actuator comprises a motor.

7. The gamma camera of claim 1, wherein the actuator is configured to move the collimator array while the detector array remains fixed.

8. The gamma camera of claim 1, wherein the collimator array comprises two collimator sub-arrays, one sub-array being proximal to the detector and one collimator sub-array being distal to the detector, a collimator of each collimator sub-array being at least partially overlapping a collimator of the other collimator sub-array, and wherein the actuator is configured to laterally displace one sub-array of the two collimator sub-arrays relative to the other.

9. The gamma camera of claim 1, further comprising a heart-lung machine to inject a radionuclide for generating the radiation into a cardioplegia blood circulation.

10. The gamma camera according to claim 1, further comprising a disposable sterile cover.

11. A method for operation of a gamma camera, the method comprising:
    moving a collimator array of a plurality of collimators relative to a detector array of a plurality of detector pixels with one or a plurality of incremental movements, each collimator of the plurality of collimators being configured to collimate a sampled portion of gamma radiation onto a detector pixel of said plurality of detector pixels, each incremental movement being smaller than a lateral dimension of a detector pixel of said plurality of detector pixels along an axis of motion so as to cause said each collimator to sample a different portion of the gamma radiation;
    using a processor, obtaining a signal from each detector pixel of said plurality of detector pixels, the signal indicative of the sampled portion of the gamma radiation incident on that detector pixel; and
    generating image data with sub-pixel resolution from the sampled signals and a position of the collimator when each signal was generated.

12. The method of claim 11, further comprising outputting the generated image data.

13. The method of according to claim 11, further comprising merging the image data with an image acquired by one or more imaging sensors.

14. The method of claim 13, wherein an imaging sensor of said one or more imaging sensors is selected from a group consisting of a complementary metal oxide semiconductor (CMOS) sensor, a charge coupled device (CCD) sensor, a near infrared sensor (NIR), and an ultrasound probe sensor.

15. The method of claim 11, wherein moving the collimator array comprises operating a motor.

16. The method of claim 11, wherein moving the collimator array comprises moving the collimator array while the detector array remains fixed.

17. The method of claim 11, wherein the collimator array comprises two collimator sub-arrays, one collimator sub-array being proximal to the detector and one collimator sub-array being distal to the detector, a collimator of each collimator sub-array being at least partially overlapping a collimator of the other collimator sub-array, and wherein moving the collimator array comprises laterally displacing one of the two collimator sub-arrays relative to the other.

18. The method of claim 11, further comprising operating a heart-lung machine to inject a radionuclide for generating the radiation into a cardioplegia blood circulation.

* * * * *